United States Patent [19]

Horn et al.

[11] Patent Number: 5,349,073
[45] Date of Patent: Sep. 20, 1994

[54] LOW-TEMPERATURE-STABLE TITANIUM CHELATES AND METHOD FOR THEIR PREPARATION

[75] Inventors: Michael Horn; Hans-Joachim Kötzsch, both of Rheinfelden, Fed. Rep. of Germany

[73] Assignee: Hüls Aktiengesellschaft, Marl, Fed. Rep. of Germany

[21] Appl. No.: 121,307

[22] Filed: Sep. 14, 1993

Related U.S. Application Data

[60] Division of Ser. No. 993,975, Dec. 15, 1992, abandoned, which is a continuation of Ser. No. 734,271, Jul. 22, 1991, abandoned.

[30] Foreign Application Priority Data

Jul. 27, 1990 [DE] Fed. Rep. of Germany ....... 4023851

[51] Int. Cl.$^5$ ................................................ C07F 7/28
[52] U.S. Cl. ..................................................... 556/54
[58] Field of Search ........................................... 556/54

[56] References Cited

U.S. PATENT DOCUMENTS

| 3,056,818 | 10/1962 | Werber | 260/410.6 |
| 3,856,839 | 12/1974 | Smith et al. | 260/429.5 |
| 4,122,062 | 10/1978 | Monte et al. | 260/42.14 |
| 4,216,107 | 8/1980 | Vogt et al. | 252/182 |
| 4,521,461 | 6/1985 | McVie et al. | 427/387 |
| 4,558,076 | 12/1985 | Wright et al. | 523/442 |
| 4,851,142 | 7/1989 | Scoggins et al. | 252/8.515 |

*Primary Examiner*—José G. Dees
*Assistant Examiner*—Porfirio Nazario-Gonzalez
*Attorney, Agent, or Firm*—Felfe & Lynch

[57] ABSTRACT

Isopropoxyalkoxytitanium bis(acetylacetonate) compounds are prepared by admixing diisopropoxytitanium bis(acetylacetonate) with a dialkoxytitanium bis(acetylacetonate), and allowing the mixture to react, optionally at elevated temperatures.

3 Claims, No Drawings

LOW-TEMPERATURE-STABLE TITANIUM CHELATES AND METHOD FOR THEIR PREPARATION

This is a division application of application Ser. No. 07/993,975, filed Dec. 15, 1992, now abandoned; which in turn is a continuation of application Ser. No. 07/734,271, filed Jul. 22, 1991, now abandoned.

FIELD OF THE INVENTION

This invention relates to novel low-temperature-stable titanium chelates as well as to a method for their preparation.

BACKGROUND OF THE INVENTION

The preparation of titanium chelates of the formula $(RO)_2TiX_2$ wherein X is acetylacetonate and R is straight or branched alkyl of 2 to 4 carbon atoms, is conventionally carried out by reacting a titanium orthoester of the formula $Ti(OR)_4$, wherein R has the meanings defined above, with two equivalents of the chelating agent acetylacetone, accompanied by the release of two equivalents of the alcohol of the formula ROH, wherein R has the meanings already defined.

For practical application, these titanium chelates are usually left in the reaction solution in which they are formed, that is, the alcohol released by the reaction is not separated. This was the only way to achieve moderate low-temperature stability of the previously used substances.

When these acetylacetonate solutions are used in industry, where very low flash points because of the alcohol content have to be accepted, the effects which were achieved often varied substantially and were therefore not satisfactory. Moreover, the alcohol released by the reaction entered the exhaust gases and/or the liquid effluence and had to be removed therefrom by expensive procedures.

After the alcohol released by the reaction is separated by distillation, viscous liquids remain, the setting points of which are, however, above $-18°$ C. or which crystallize spontaneously within a short period of time, even at room temperature, and thus become useless.

OBJECTS OF THE INVENTION

It is an object of the present invention to provide titanium chelate products which can be easily and safely handled and produce a reliably good effect, especially for the treatment of surfaces.

Another object is to lower the solvent content of the titanium chelate products.

Still another object of the present invention is to provide a process for the preparation of titanium chelate products which reduces the environmental pollution impact.

Other objects and advantages of the present invention will become apparent as the description thereof proceeds.

DESCRIPTION OF THE INVENTION

The above objects are achieved by providing titanium chelates of the formula

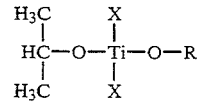

wherein X is

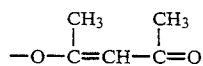

R is ethyl, n-propyl, n-butyl, isobutyl or tert.-butyl, as well as a novel process for the preparation of these compounds.

The titanium chelates of the instant invention have a surprisingly very low setting point and do not exhibit the disadvantages of the prior art products described above. The products obtained in accordance with the present invention are useful for improving the adhesion of printing inks to inorganic surfaces, and for coating plate glass, hollow glassware and glass fibers for improving their mechanical and optical properties.

The previously used processes for the preparation of titanium acetylacetonates having variable alkoxy radicals attached to the titanium atom, such as, for example, mixing of the titanium orthoesters $(isopropoxy)_4Ti$ and $(RO)_4Ti$, reacting this mixture with the chelating agent acetylacetone, and removing the alcohol released by the reaction by distillation; or mixing one of the starting chelates $(R'O)_2TiX_2$ with the titanium orthoester $(R''O)_4Ti$, where R' is R or isopropyl, R'' is R or isopropyl but R' is different from R'' reacting this mixture with the chelating agent acetylacetone, and removing the alcohol released by the reaction by distillation, do not produce the uniform products defined by formula I above which have the stoichiometry predetermined by the ratio of the titanium compounds which are used to prepare them. The prior art processes merely lead to non-uniform solutions of mixed titanium chelates having very different compositions and the undesirable properties resulting therefrom.

The titanium chelates of the instant invention defined by formula I above have not previously been prepared in pure form.

The titanium chelates $(R'O)_2TiX_2$ which are used as starting compounds for the process of the present invention are prepared separately in a preceding reaction in known manner, that is, by mixing a corresponding titanium orthoester $Ti(OR')_4$ with the chelating agent acetylacetone, and distilling off the alcohol R'OH formed by the reaction. The reactants are then caused to react with one another at a temperature between 20° and 100° C., preferably 1° to 30° C., above the melting point of the higher-melting-point reactant.

Spectroscopic and chromatographic analyses of the reaction mixture clearly show that the starting chelate is no longer present as such in the reaction product and that the desired end product has been formed pursuant to the equation

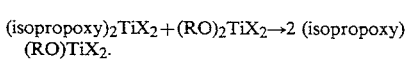

If it is desired that the end product with respect to the alkyl groups R and isopropyl in the molecule have a composition which differs from the 1:1 ratio, one of the reactants can be provided in the appropriate excess amount, for instance in a molar ratio of 1:0.1 to 1:1.9, in the above described reaction. This procedure results in mixtures of the titanium chelate (isopropoxy) (RO)TiX$_2$ with an excess of the titanium chelate (R'O)$_2$TiX$_2$, which are also obtained by admixing the mixed titanium chelate (isopropoxy) (RO)TiX$_2$ with additional starting chelate (R'O)$_2$TiX$_2$. R, R' and X in these formulas have the meanings previously defined.

Only the process of the present invention ensures that the reaction product always has the preselected stoichiometric composition. The process also ensures that the alcohol R'OH released by the reaction is separated and thus recovered in non-contaminated form, so that it can be recycled into the synthesis of the basic titanates Ti(OR')$_4$ and is not lost in a manner which pollutes the environment.

The following examples illustrate the present invention and will enable others skilled in the art to understand it more completely. It should be understood, however, that the invention is not limited solely to the particular examples given below.

EXAMPLE 1

In a first reaction vessel, 200 g of acetylacetone were added dropwise, while cooling, to 284 g of titanium tetraisopropoxide, and the resulting mixture was stirred for half an hour. Thereafter, the liberated isopropanol (120 g) was completely distilled off. The residue, diisopropoxytitanium bis(acetylacetonate), had a setting point of −18° C.

In a separate reaction vessel, 340 g of titanium tetra-n-butoxide were reacted in analogous manner with 200 g of acetylacetone, and 148 g of n-butanol were distilled off. The reaction product, di-n-butoxytitanium bis(acetylacetonate), if not immediately further processed, formed crystals having edges several centimeters in length at room temperature.

The residue of the first distillation, diisopropoxytitanium bis(acetylacetonate), was admixed with the residue of the second distillation, di-n-butoxytitanium bis(acetylacetonate), and the mixture was stirred at room temperature for 30 minutes. The reaction product, isopropoxy-n-butoxytitanium bis(acetylacetonate) had a setting point of −42° C.

EXAMPLE 2

In a first reaction vessel, solvent-free diisopropoxytitanium bis(acetylacetonate) was prepared from 284 g of titanium tetraisopropoxide and 200 g of acetylacetone as described in Example 1. A separate reaction vessel was charged with 228 g of titanium tetraethoxide. 200 g of acetylacetone were added dropwise, while cooling, and 92 g of ethanol were then distilled off. The residue, diethoxytitanium bis(acetylacetonate) crystallized if the sump temperature in the distillation flask toward the end of the distillation was allowed to drop below 35° C. and melted again at 44° to 50° C. The diisopropoxytitanium bis(acetylacetonate) from the first reaction vessel was added to the diethoxytitanium bis(acetylacetonate) from the second reaction vessel at 60° C., and the resulting mixture was maintained at 60° C. for 30 minutes more. The reaction product, ethoxyisopropoxytitanium bis(acetylacetonate) had a setting point of −33° C. and was formed quantitatively.

The following example demonstrates the adhesion improving effect of a compound of the present invention as an additive to a nitrocellulose lacquer.

EXAMPLE 3

A nitrocellulose white lacquer containing 25% nitrocellulose was admixed with 1% by weight of isopropoxy-n-butoxytitanium bis(acetylacetonate). The mixture was applied with the aid of a knife to one half of a degreased sheet of polypropylene, while a sample of the nitrocellulose white lacquer without the titanium chelate additive was applied in the same manner to the other half of the polypropylene sheet. The sheet was then dried in the air for 5 minutes. An adhesive strip was then applied horizontally to each half of the treated polypropylene sheet, and the strips were pulled off in one fell swoop beginning at opposite ends. A comparison of the two sheet halves showed that more than 95% of the lacquer without the additive was removed from the sheet, but only about 50% of the lacquer containing the titanium chelate additive of the present invention was removed.

COMPARATIVE EXAMPLE 284 g of titanium tetraisopropoxide and 340 g of titanium tetra-n-butoxide were admixed with each other, and 400 g of acetylacetone were added dropwise thereto. The alcohol released by the reaction was distilled off. This mixture of isopropanol and n-butanol could not be separated into its components in a cost-effective manner and had to be destroyed. Furthermore, the composition of the alcohol mixture was dependent upon the change in pressure during the distillation and was therefore difficult to reproduce. This deficiency also had an effect on the composition of the end product, as evidenced by the TiO$_2$ content which varied between 19.5 and 22.5% in several experiments.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing a compound of the formula

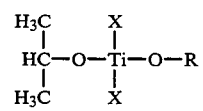

wherein X is

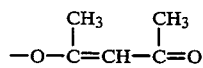

and R is ethyl, n-propyl, n-butyl, isobutyl or tert.-butyl, which comprises admixing a compound of the formula (isopropoxy)$_2$TiX$_2$ with a compound of the formula (RO)$_2$TiX$_2$, wherein R and X have the meanings defined above, in a molar ratio of 1:1 in the liquid phase, and allowing the mixture to react at a temperature between 20° and 100° C. above the melting point of the higher-melting-point reactant for 0 to 60 minutes.

2. The method of claim 1, wherein the mixture is allowed to react thermally at a temperature between 1° to 30° C. above the melting point of the higher-melting-point reactant for 30 minutes.

3. The method of claim 1, wherein the said compounds are admixed in molar ratios of 1:0.1 to 1:1.9.

* * * * *